United States Patent [19]

Sih

[11] 4,301,079
[45] Nov. 17, 1981

[54] 19-HYDROXY-19-METHYL-PGI$_1$ COMPOUNDS

[75] Inventor: John C. Sih, Kalamazoo, Mich.

[73] Assignee: The Upjohn Company, Kalamazoo, Mich.

[21] Appl. No.: 126,503

[22] Filed: Mar. 3, 1980

Related U.S. Application Data

[62] Division of Ser. No. 54,720, Jul. 5, 1979, Pat. No. 4,225,507.

[51] Int. Cl.$^3$ .......................................... C07D 307/935
[52] U.S. Cl. ............................. 260/346.22; 542/416; 542/420; 542/421; 542/426; 548/252; 260/346.73
[58] Field of Search ...................... 260/346.22, 346.73; 542/416, 420, 421, 426; 548/252

[56] References Cited

U.S. PATENT DOCUMENTS

3,878,046  4/1975  Marsheck et al. ................. 562/503
4,054,595 10/1977  Marx et al. ......................... 562/503

FOREIGN PATENT DOCUMENTS

862514  4/1978  Belgium ......................... 260/346.22
777401 12/1977  South Africa .

Primary Examiner—Henry R. Jiles
Assistant Examiner—Bernard Dentz
Attorney, Agent, or Firm—L. Ruth Hattan; Robert A. Armitage

[57] ABSTRACT

The present invention provides novel 19-Hydroxy-19-methyl-PGI$_1$ compounds which are useful for pharmacological purposes, e.g., anti-asthmatic indications.

4 Claims, No Drawings

4,301,079

19-HYDROXY-19-METHYL-PGI$_1$ COMPOUNDS

CROSS REFERENCE TO RELATED APPLICATION

The present invention is a divisional application of U.S. Ser. No. 54,720, filed July 5, 1979 now U.S. Pat. No. 4,225,507.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-19-methyl-PGI$_1$ compounds. The novel prostacyclin analogs are useful for pharmacological purposes, e.g., as anti-asthmatic agents. The preparation and use of these compounds is incorporated here by reference from U.S. Ser. No. 54,720, filed July 5, 1979.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J. C. S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI$_2$, see R. A. Johnson, et al., Prostaglandins 15, 737–740 (1978).

SUMMARY OF THE INVENTION

The present invention particularly provides a prostacyclin-type compound of the formula

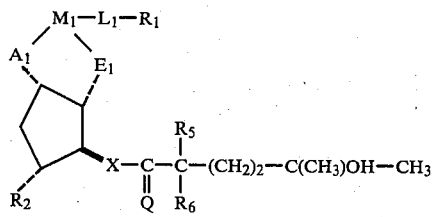

wherein A$_1$ is —O— (oxa) and E$_1$ is —CH$_2$
wherein L$_1$ is
(1) —(CH$_2$)$_n$—, wherein n is one to 5, inclusive,
(2) —(CH$_2$)$_p$—CF$_2$—, wherein p is 2, 3, or 4, or
(3) —CH$_2$—CH=CH—;
wherein M$_1$ is

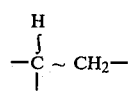

wherein Q is oxo, α-H:β-H, α-OH:β-R$_4$, or α-R$_4$:β-OH,
wherein R$_4$ is hydrogen or alkyl of one to 4 carbon atoms, inclusive,
wherein R$_1$ is
(1) —COOR$_3$,
(2) —CH$_2$OH,
(3) —CH$_2$N(R$_7$)(R$_8$),
(4) —CO—N(R$_7$)(R$_8$),
(5) —CO—NH—SO$_2$—R$_{15}$, or
(6) tetrazolyl,
wherein R$_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive;
(g) —(p-Ph)—CO—CH$_3$,
(h) —(p-Ph)—NH—CO—(p-Ph)—NH—CO—CH$_3$,
(i) —(p-PH)—NH—CO—(Ph),
(j) —(p-Ph)—NH—CO—CH$_3$,
(k) —(p-Ph)—NH—CO—NH$_2$,
(l) —(p-Ph)—CH—NH—NH—CO—NH$_2$,
(m) β-naphthyl,
(n) —CH$_2$—CO—R$_{16}$,
wherein —(p-Ph)— is para-phenylene and —(Ph) is phenyl;
wherein R$_{16}$ is phenyl, p-bromophenyl, p-biphenylyl, p-nitrophenyl, p-benzamidophenyl, or 2-naphthyl, or
(o) a pharmacologically acceptable cation; wherein R$_7$ and R$_8$ are hydrogen, alkyl of one to 12 carbon atoms, inclusive, benzyl, or phenyl, being the same or different, and wherein R$_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive,
wherein R$_2$ is hydrogen, hydroxyl, or hydroxymethyl,
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and
wherein X is
(1) trans-CH=CH—,
(2) cis-CH=CH—,
(3) —C≡C—, or
(4) —CH$_2$CH$_2$—.

DESCRIPTION OF THE PREFERRED EMBODIMENTS

The present invention particularly relates to the following compounds:
2-Decarboxy-2-hydroxymethyl-9-deoxy-6ξ, 9α-epoxy-19-hydroxy-19-methyl-PGF$_1$, and
2-Decarboxy-2-hydroxymethyl-9-deoxy-6ξ, 9α-epoxy-16,16-difluoro-19-hydroxy-19-methyl-PGF$_1$.

I claim:
1. A prostacyclin-type compound of the formula

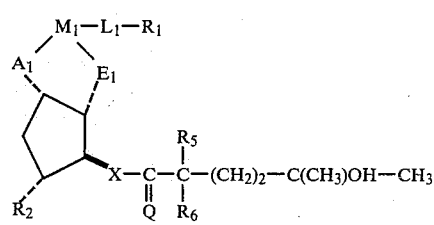

wherein A$_1$ is —O— (oxa) and E$_1$ is —CH$_2$ wherein L₁ is
(1) —(CH₂)ₙ—, wherein n is one to 5, inclusive,
(2) —(CH₂)ₚ—CF₂—, wherein p is 2, 3, or 4, or
(3) —CH₂—CH=CH—;
wherein M₁ is

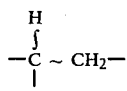

wherein Q is oxo, α-H:β-H, α-OH:β-R₄, or α-R₄:β-OH,
wherein R₄ is hydrogen or alkyl of one to 4 carbon atoms, inclusive,
wherein R₁ is
(1) —COOR₃,
(2) —CH₂OH,
(3) —CH₂N(R₇)(R₈),
(4) —CO—N(R₇)(R₈),
(5) —CO—NH—SO₂—R₁₅, or
(6) tetrazolyl,
wherein R₃ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive;
(g) —(p-Ph)—CO—CH₃,
(h) —(p-Ph)—NH—CO—(p-Ph)—NH—CO—CH₃,
(i) —(p-Ph)—NH—CO—(Ph),
(j) —(p-Ph)—NH—CO—CH₃,
(k) —(p-Ph)—NH—CO—NH₂,
(l) —(p-Ph)—CH=N—NH—CO—NH₂,
(m) β-napthyl,
(n) —CH₂—CO—R₁₆,
wherein —(p-Ph)— is para-phenylene and —(Ph) is phenyl;
wherein R₁₆ is phenyl, p-bromophenyl, p-biphenyl, p-nitrophenyl, p-benzamidophenyl, or 2-napthyl, or
(o) a pharmacologically acceptable cation; wherein R₇ and R₈ are hydrogen, alkyl of one to 12 carbon atoms, inclusive, benzyl, or phenyl, being the same or different, and wherein R₁₅ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive,
wherein R₂ is hydrogen, hydroxyl, or hydroxymethyl,
wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro, and
wherein X is
(1) trans—CH=CH—,
(2) cis-CH=CH—,
(3) —C≡C—, or
(4) —CH₂CH₂—;
with the proviso that when L₁ is —(CH₂)ₙ— and R₁ is other than —CH₂NR₇R₈ or —CONHSO₂R₁₅, one of R₅ and R₆ is other than hydrogen.

2. A compound according to claim 1, wherein R₁ is —CH₂OH.

3. A compound according to claim 2, wherein L₁ is —(CH₂)₃—, Q is α-OH:β-H, R₂ is hydroxyl, and X is trans-CH=CH—.

4. 2-Decarboxy-2-hydroxymethyl-9-deoxy-6ξ,9α-epoxy-16,16-difluoro-19-hydroxy-19-methyl-PGF₁, a compound according to claim 2.

* * * * *